United States Patent [19]

Frecon

[11] Plant 4,901

[45] Oct. 26, 1982

[54] SPUR TYPE WINTER BANANA APPLE TREE—FRECON CULTIVAR

[75] Inventor: Richard S. Frecon, Boyertown, Pa.

[73] Assignee: Stark Brothers Nurseries & Orchards Company, Louisiana, Mo.

[21] Appl. No.: 224,628

[22] Filed: Jan. 12, 1981

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

A new and distinct spur type apple variety which originated as a limb mutation of the standard winter banana apple tree (non-patented) is provided. This new apple variety possesses a vigorous compact and only slightly spreading growth habit and can be distinguished from its parent and the Housden spur type winter banana apple variety (non-patented). More specifically, the new variety forms more fruiting spurs per unit length on two and three year old wood than the standard winter banana apple tree and less spurs per unit length than the Housden spur type winter banana apple tree. Additionally, the new variety has the ability to heavily bear fruit having a whitish-yellow skin color with a sometimes slight scarlet red blush upon maturity which is substantially identical to that of the standard winter banana apple tree and which has substantially less skin russeting than the Housden spur type winter banana apple tree.

5 Drawing Figures

SUMMARY OF THE INVENTION

Banana apple trees long have been known and have received their name from the faint banana aroma or flavor of the fruit. Such trees not only produce all-purpose apples, but are recognized to be excellent pollinators for red delicious apple trees.

The new and distinct banana apple variety of the present invention was discovered by me during August 1978 while growing as a limb mutation in my cultivated orchard near Boyertown, Colebrookdale Township, Berks County, Pa. More specifically, the limb mutation was discovered on a tree of the standard winter banana apple tree (non-patented).

I was originally attracted to the limb mutation by its distinctive growth habit whereby moderately heavy to heavy quantities of fruit spurs are borne on two and three year old wood. Continued observation and testing has indicated that this discovery is in fact a new variety and differs from all previously known banana apple varieties of which I am aware.

It has been found that fruit on the new variety is borne on shorter and heavier fruiting spurs which are more closely spaced and in greater numbers than found on the standard winter banana apple tree. The fruit production on the new variety begins at an early age if good horticultural practices are followed. Also, because of the slightly spreading tendency the new variety is better able to sustain heavy crops of fruit without breakage.

The new variety of banana apple tree possesses the following combination of characteristics:

(a) a vigorous compact growth habit with only a slightly spreading tendency, (b) the ability to heavily bear fruit having a whitish-yellow skin color upon maturity which is substantially identical to that of a standard winter banana apple tree and which has substantially less skin russeting than the fruit of the Housden spur type winter banana apple tree, (c) the ability to form large long green leaves, and (d) the propensity to form more fruit spurs per unit length of two and three year old wood than the standard winter banana apple tree and less spurs per unit length than the Housden spur type winter banana apple tree.

Asexual propagation beginning at Louisiana, Mo. in September, 1978, has demonstrated that the unique combination of characteristics of this new variety comes true to form and is established and transmitted through succeeding propagations.

All specimens described herein were grown at my orchard near Boyertown, Pa.

The new variety has been named the Frecon Cultivar.

BRIEF DESCRIPTION OF THE PHOTOGRAPHS

The subject matter of the photographs was obtained during July, 1980 near Boyertown, Pa., and is presented in color as true as reasonably possible in an illustration of this character.

DETAILED DESCRIPTION OF THE NEW VARIETY

Figures 1, 2, 3:
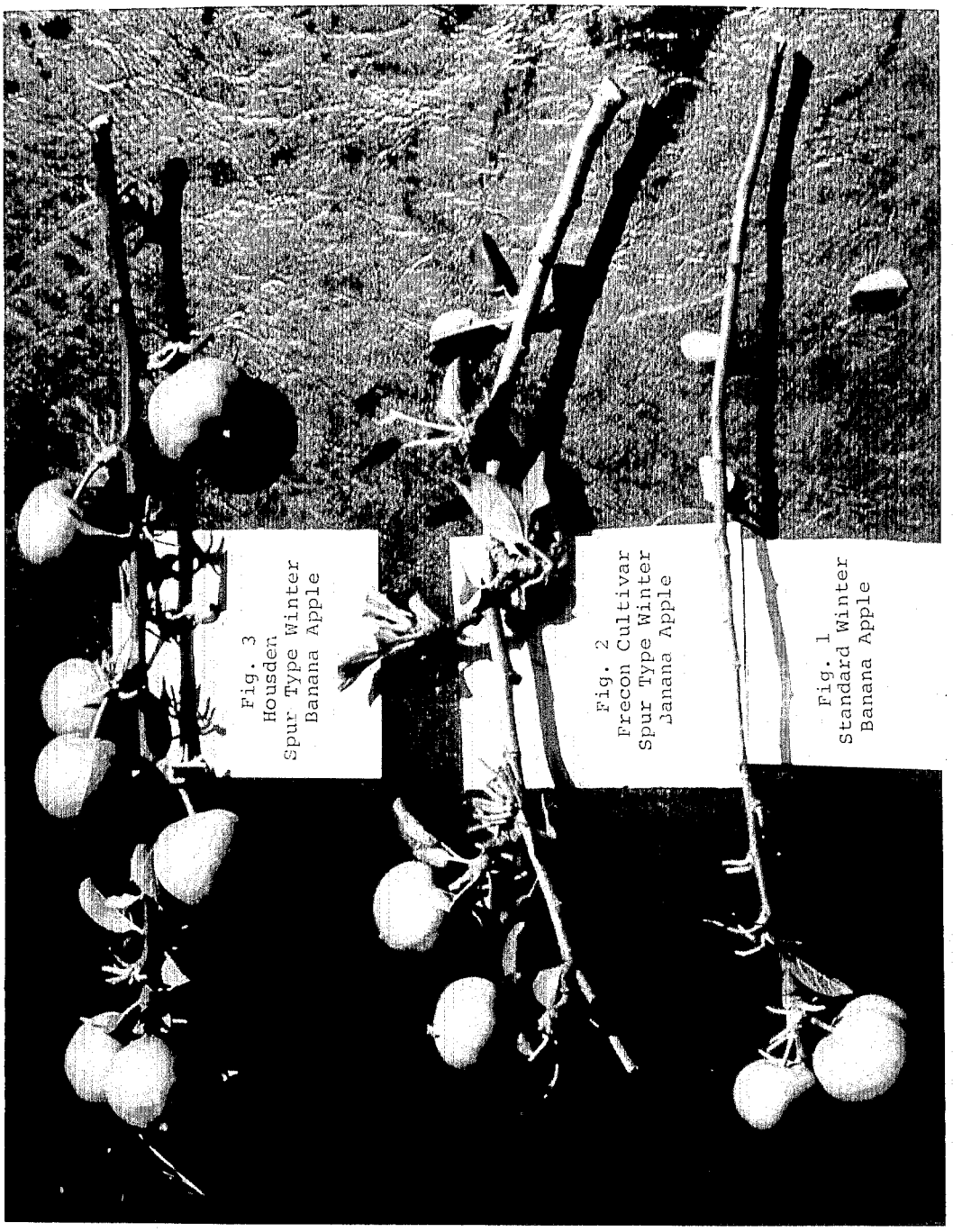
FIG. 1 shows a typical bearing shoot of the standard winter banana apple tree which is substantially free of fruit spurs.
FIG. 2 shows a typical bearing shoot of the Frecon Cultivar of the present invention which exhibits a greater number of fruit spurs than the standard winter banana apple tree of FIG. 1 and a lesser number of fruit spurs than the Housden spur type winter banana apple tree of FIG. 3. One spur is present for each approximately one to eight inches of bearing shoot.
FIG. 3 shows a typical bearing shoot of the Housden spur type winter banana apple tree which bears a greater number of fruit spurs than the Frecon Cultivar of FIG. 2. One spur is present for each approximately one to five inches of bearing shoot.
Figures 4, 5:
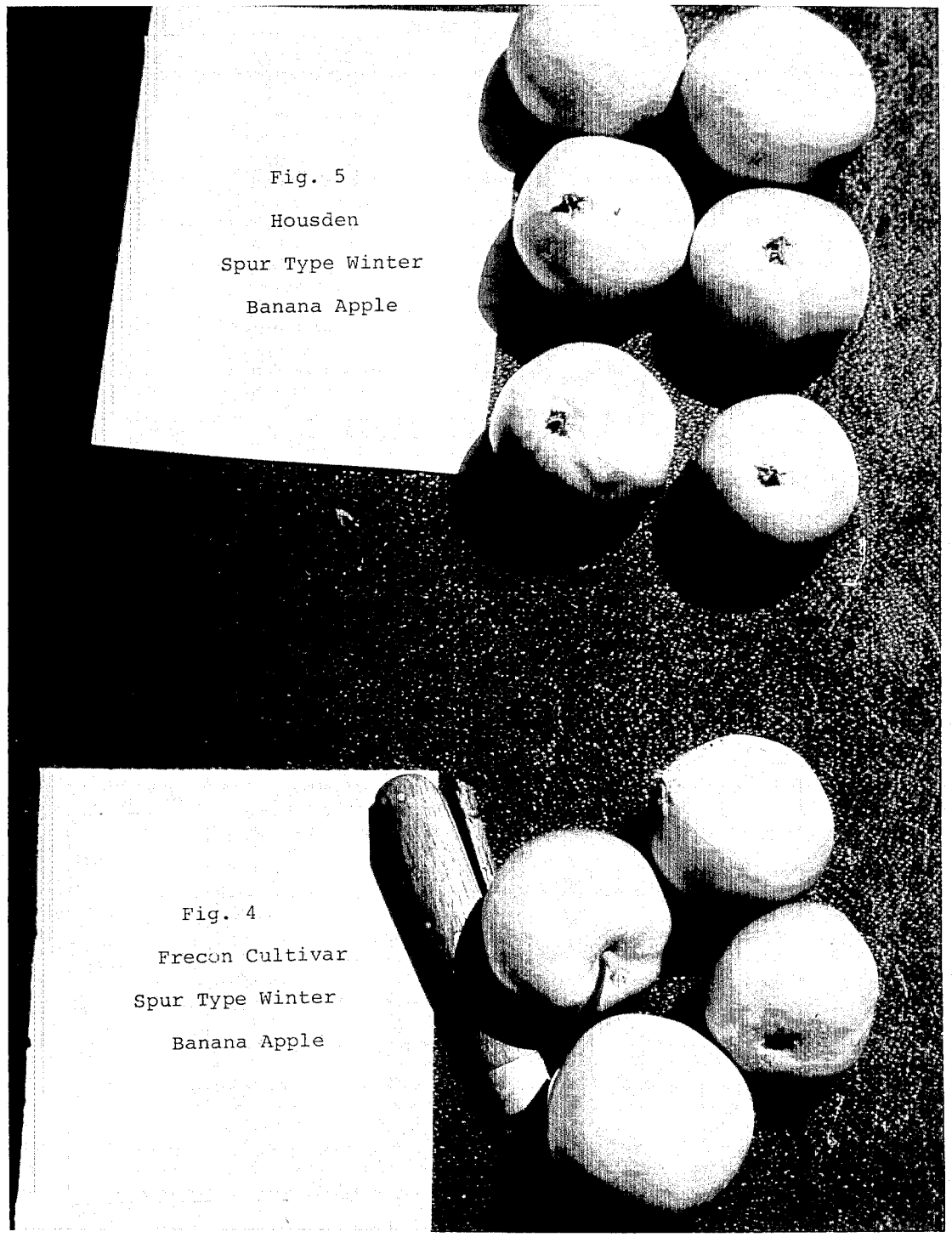
FIG. 4 shows typical fruit of the Frecon Cultivar of the present invention which is substantially free of skin russeting.
FIG. 5 shows typical fruit of the Housden spur type winter banana apple tree in which a substantial amount of the usual skin russeting is apparent on the upper apples.

The following is a detailed description of my new variety where color terminology is to be accorded its ordinary dictionary significance except where otherwise indicated. The specimens described were grown near Boyertown, Pa.

Dates of first and last pickings—Oct. 1, 1980 and Oct. 15, 1980 in Pennsylvania; the dates are commonly the same as those of the standard winter banana apple tree (non-patented) and the Housden spur type winter banana apple tree (non-patented).

Tree: Medium; vigorous; upright & spreading; low; vase-formed; slow growing; hardy; very productive; regular bearing.

*Trunk.*—Medium stocky; medium smooth.

*Branches.*—Medium thick; much branching; reddish brown.

*Lenticels.*—Numerous; medium large.

*Leaves.*—Length — approximately 4 inches; width — approximately 2½ inches; large; medium wide; long; ovate; taper — pointed; medium thick; medium green; rugose; margin — finely serrate.

*Petiole.* —Length — approximately 1 3/16 inch; medium long; medium slender.

Flowers: Date of first bloom May 15 to 10, 1980, medium early — similar to Red Delicious apple; large, white.

Fruit: Maturity date when eating ripe — Oct. 15, 1980.

*Size.*—Variable — axial diameter — approximately 2 11/16 inch; transverse — approximately 3 inches.

*Cavity.*—Acute to acuminate; gently furrowed; sometimes full to partly russeted; sometimes lipped; depth — approximately 9/16 inch; breadth — approximately 1½ inch.

*Basin.*—Obtuse to abrupt at base; furrowed to wrinkled; oblique; depth — approximately ⅜ inch; breadth — approximately 1½ inch.

*Stem.*—Slender to medium; slighty pubescent; length — approximately ½ inch; breadth — approximately 1/16 inch.

*Calyx.*—Partly open; deciduous; obtuse to acute; mostly connivent.

*Eye.*—Medium.

*Skin.*—Moderately thick; tough; smooth; waxed; many submerged dots. Color of dots — Whitish with fine russet dots. Ground color — Ridgway Color Standards Plate IV — Martius yellow to Piric yellow. Color markings — Blushed. Bloom — Wanting. General color effect — Light pale yellow as is ground color — sometimes have blush similar to Ridgway Color Standards Plate 1 — Spectrum Red.

*Flesh.*—White with yellowish tint. Texture — Moderately firm; tender, coarse; and crisp. Flavor — Subacid. Aroma — Pronounced. Quality — Good. Aromatic slighty like banana.

*Core.*—Abaxile; medium-to-small. Halves of area — Unequal. Bundles — Green-yellowish. Core lines — Clasping. Calyx-tube — Glabrous. Stamens — Distinct whorls. Auxiliary cavity — Present. Surface — Slightly tufted.

*Seeds.*—Number perfect — 8; Number imperfect — often aborted. Number in one cell — 1 to 2. Breadth — ⅛ inch to ¼ inch. Form — Obtuse to acute. Color — dull — dark brown sometimes.

Use: Local market; variety excellent pollinator for Red Delicious apple.

Keeping quality: Medium.

*Number of days in ordinary storage.*—120.

Resistance to:

*Insects.*—Medium.

*Diseases.*—*Medium.*

I claim:

1. A new and distinct variety of winter banana apple tree, substantially as illustrated and described, characterized by (a) a vigorous compact upright growth habit with only a slightly spreading tendency, (b) the ability to heavily bear fruit having a whitish-yellow skin color upon maturity which is substantially identical to that of the standard winter banana apple tree and which has substantially less skin russeting than the fruit of the Housden spur type winter banana apple tree, (c) the ability to form large long green leaves, and (d) the propensity to form more fruit spurs per unit length of two and three year old wood than the standard winter banana apple tree and less spurs per unit length of two and three year old wood than the Housden spur type winter banana apple tree.

* * * * *

Housden
Spur Type Winter
Banana Apple

Frecon Cultivar
Spur Type Winter
Banana Apple

Standard Winter
Banana Apple

Housden
Spur Type Winter
Banana Apple

Frecon Cultivar
Spur Type Winter
Banana Apple